US012636340B2

(12) United States Patent
Klippel

(10) Patent No.: US 12,636,340 B2
(45) Date of Patent: May 26, 2026

(54) METHODS OF TREATING MULTIPLE MYELOMA

(71) Applicants: ONYX PHARMACEUTICALS, INC., Thousand Oaks, CA (US); Janssen Biotech, Inc., Horsham, PA (US)

(72) Inventor: Zandra Klippel, Newbury Park, CA (US)

(73) Assignees: ONYX PHARMACEUTICALS, INC., Thousand Oaks, CA (US); Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 17/243,863

(22) Filed: Apr. 29, 2021

(65) Prior Publication Data

US 2021/0338766 A1      Nov. 4, 2021

Related U.S. Application Data

(60) Provisional application No. 63/017,336, filed on Apr. 29, 2020.

(51) Int. Cl.
| | |
|---|---|
| *A61P 35/00* | (2006.01) |
| *A61K 31/573* | (2006.01) |
| *A61K 38/07* | (2006.01) |
| *A61K 39/395* | (2006.01) |
| *A61K 39/00* | (2006.01) |

(52) U.S. Cl.
CPC ............ *A61K 38/07* (2013.01); *A61K 31/573* (2013.01); *A61K 39/3955* (2013.01); *A61P 35/00* (2018.01); *A61K 2039/505* (2013.01); *A61K 2039/545* (2013.01)

(58) Field of Classification Search
CPC .. A61K 38/07; A61K 31/573; A61K 39/3955; A61K 2039/505; A61K 2039/545; A61P 35/00
See application file for complete search history.

(56) References Cited

U.S. PATENT DOCUMENTS

| | | | | |
|---|---|---|---|---|
| 10,385,135 | B2 * | 8/2019 | Jansson | A61K 47/26 |
| 10,781,261 | B2 * | 9/2020 | Jansson | C07K 16/2896 |
| 2015/0246123 | A1 * | 9/2015 | Doshi | A61P 43/00 424/139.1 |
| 2018/0117150 | A1 * | 5/2018 | O'Dwyer | A61K 39/39558 |
| 2019/0127479 | A1 * | 5/2019 | Ahmadi | A61P 35/00 |
| 2019/0298827 | A1 | 10/2019 | Xie et al. | |

OTHER PUBLICATIONS

Jakubowiak et al (Daratumumab (DARA) in combination with carfilzomib, lenalidomide, and dexamethasone (KRd) in patients (pts) with newly diagnosed multiple myeloma (MMY1001): An open-label, phase 1b study, Journal of Clinical Oncology 35, No. 15_suppl (May 20, 2017) pp. 8000-8000) (Year: 2017).*

Chari et al (Daratumumab plus carfilzomib and dexamethasone in patients with relapsed or refractory multiple myeloma, The American Society of Hematology, Blood, 2019, V. 134, No. 5, pp. 421-431) (Year: 2019).*
Dimopoulos et al (Carfilzomib and dexamethasone versus bortexomib and dexamethasone for patients with relapsed or refractory multiple myeloma (ENDEAVOR): a randomized, phase 3, open-label, multicetre study, Lancet Oncol, 2016, 17, pp. 27-38) (Year: 2016).*
Helwick (Addition of Daratumumab Increases Benefit of Carfilzomib/Dexamethasone in Multiple Myeloma, ASCO Post, Dec. 2019) (Year: 2019).*
Attal, et al; IFM Investigators. Lenalidomide maintenance after stem-cell transplantation for multiple myeloma. N Engl J Med, 2012;366:1782-91.
Chari et al., Daratumamab (DARA) in combination with carfilzomib and dexamethasone (D-Kd) in lenalidomide (Len)-refractory patients (Pts) with relapsed multiple myeloma (MM): subgroup analysis of MMY1001, J. Clin. Oncol., 36 (15 suppl):80002 (May 2018).
Chari et al., Daratumumab (DARA) in combination with carfilzomib, lenalidomide, and dexamethasone (KRd) in patients with newly diagnosed multiple myeloma (MMY1001): updated results from an open-label, phase 1b study, Blood, 130:3110 (2017).
Chari et al., Daratumumab plus carfilzomib and dexamethasone in patients with relapsed or refractory multiple myeloma, Blood, 134(5):421-31 (2019).
Chari et al., Final analysis of a phase 1b study of Daratumumab in combination with carfilzomib and dexamethasone for relapsed or refractory multiple myeloma (RRMM), Blood, vol. 134, 6 pp. (2019).
Costa et al., Daratumumab carfilzomib, lenalidomide and dexamethasone (Dara-KRd) induction, autologous transplantation and post-transplant, response-adapted, measurable residual disease (MRD)-based Dara-Krd consolidation in patients with newly diagnosed multiple myeloma (NDMM), Blood, 134:860 (2019).
Darzalex™ (daratumumab) injection, for intravenous use [package insert]. Horsham, PA: Janssen Biotech, Inc.; 2018.
Dimopoulos et al., Carfilzomib or bortezomib in relapsed or refractory multiple myeloma (ENDEAVOR): an interim overall survival analysis of an open-label, randomised, phase 3 trial, Lancet Oncol., 18(10):1327-37 (2017).
Dimopoulos et al., Carfilzomib, dexamethasone, and daratumumab versus carfilzomib and dexamethasone for patients with relapsed or refractory multiple myeloma (CANDOR): results from a randomised, multicentre, open-label, phase 3 study, Lancet, 396(10245):186-97 (2020).
Dimopoulos et al., Daratumumab, Lenalidomide, and Dexamethasone for Multiple Myeloma, N. Engl. J. Med., 375(14):1319-31 (2016).

(Continued)

*Primary Examiner* — Nelson B Moseley, II
*Assistant Examiner* — Dennis J Sullivan
(74) *Attorney, Agent, or Firm* — MARSHALL, GERSTEIN & BORUN LLP

(57) ABSTRACT

Provided herein are methods of treating a subject suffering from multiple myeloma by administering a triplet therapy of carfilzomib, dexamethasone, and an antibody that specifically recognizes CD38.

18 Claims, 2 Drawing Sheets

Specification includes a Sequence Listing.

(56) References Cited

OTHER PUBLICATIONS

Dimopoulos, et al. Carfilzomib and dexamethasone versus bortezomib and dexamethasone for patients with relapsed or refractory multiple myeloma (ENDEAVOR): a randomised, phase 3, open-label, multicentre study, Lancet Oncol, 2016;17:27-38.

Dimopoulos, et al; POLLUX Investigators. Daratumumab, lenalidomide, and dexamethasone for multiple myeloma, N Engl J Med, 2016;375:1319-31.

Drayson, et al. Levofloxacin prophylaxis in patients with newly diagnosed myeloma (TEAMM): A multicenter, double-blind, placebo-controlled, randomised, phase 3 trial. Lancet Oncol, 2019;20:1760-1772.

European Medicines Agency. Kyprolis: Product Information. London, UK: EMA; 2016.

Facon, et al. Final analysis of survival outcomes in the phase 3 FIRST trial of up-front treatment for multiple myeloma, Blood, 2018;131:301-10.

International Application No. PCT/US2021/029830, International Search Report and Written Opinion, mailed Jul. 28, 2021.

Kazandjian, et al. Remission and progression-free survival in patients with newly diagnosed multiple myeloma treated with carfilzomib, lenalidomide, and dexamethasone: five-year follow-up of a phase 2 clinical trial, JAMA Oncol, 2018;4:1781-3.

Kumar, et al. Improved survival in multpile myeloma and the impact of novel therapies, Blood, 2008;111:2516-20.

Kumar, et al. International Myeloma Working Group consensus criteria for response and minimal residual disease assessment in multiple myeloma, Lancet Oncol, 2016;17:e328-46.

Kyprolis® (carfilzomib) [package insert]. Thousand Oaks, CA: Amgen, Inc.; 2018.

Lonial et al., Daratumumab in combination with carfilzomib and dexamethasone in patients (pts) with relapsed multiple myeloma (MMY1001): An open-label, phase 1b study, Blood, 130:1869 (2017).

Lonial et al., Myeloma Is Not a Single Disease, J. Oncol. Pract., 12(4):287-92 (2016).

Martinez-Lopez, et al. Prognostic value of deep sequencing method for minimal residual disease detection in multiple myeloma, Blood, 2014;123:3073-9.

McCarthy, et al. Lenalidomide maintenance after autologous stem-cell transplantation in newly diagnosed multiple myeloma: a meta-analysis, J Clin Oncol, 2017;35:3279-89.

Moreau et al., Isatuximab plus carfilzomib/dexamethasone versus carfilzomib/dexamethasone in patients with relapsed/refractory multiple myeloma: IKEMA Phase III study design, Future Oncol., 16(2):4347-58 (2020).

Moreau, et al. Impact of prior treatment on patients with relapsed multiple myeloma treated with carfilzomib and dexamethasone vs bortezomib and dexamethasone in the phase 3 ENDEAVOR study, Leukemia, 31:115-122.

Moreau, et al. Once weekly versus twice weekly carfilzomib dosing in patients with relapsed and refractory multiple myelom (A.R.R.O.W.): interim analysis results of a randomised, phase 3 study. Lancet Oncol, 2018;19:953-64.

Moreau, et al. Treatment of patients with multiple myeloma progressing on frontline-therapy with lenalidomide, Blood Cancer J, 2019;9:38.

Nijhof, et al. Current and new therapeutic strategies for relapsed and refractory multiple myeloma: an update, Drugs, 2018;78:19-37.

Obeng, et al. Proteasome inhibitors induce a terminal unfolded protein response in multiple myeloma cells, Blood, 2006;107:4907-16.

Overdijk, et al. Antibody-mediated phagocytosis contributes to the anti-tumor activity of the therapeutic antibody daratumumab in lymphoma and multiple myeloma, MAbs, 2015;7:311-21.

Palumbo et al., Geriatric assessment predicts survival and toxicities in elderly myeloma patients: an International Myeloma Working Group report, Blood, 125(13):2068-74 (2015).

Palumbo et al., Phase III randomized controlled study of daratumumab, bortezomib, and dexamethasone (DVd) versus bortezomib and dexamethasone (Vd) in patients with relapsed or refractory multiple myeloma (RRMM): CASTOR study, J. Clin. Oncol., 34(suppl): abstract LBA4 (2016).

Palumbo, et al; CASTOR Investigators. Daratumumab, bortezomib, and dexamethasone for multiple myeloma, N Engl J Med, 2016;375:754-66.

Paquin et al. Overall survival of transplant eligible patients with newly diagnosed multiple myeloma: comparative effectiveness analysis of modern induction regimens on outcome, Blood Cancer J, 2018;8:125.

Pulte, et al. FDA approval summary: Lenalidomide as maintenance therapy after autologous stem cell transplant in newly diagnosed multiple myeloma, Oncologist, 2018;23:734-9.

Richardson, et al; OPTIMISMM Trial Investigators. Pomalidomide, bortezomib, and dexamethasone for patients with relapsed or refractory multiple myeloma previously treated with lenalidomide (OPTIMISMM): a randomised, open-label, phase 3 trial; Lancet Oncol, 2019; 20:781-94.

Schemper et al., A note on quantifying follow-up in studies of failure time, Control. Clin. Trials, 17(4):343-6 (1996).

Sonneveld et al. How have evolutions in strategies for the treatment of relapsed/refractory multiple myeloma translated into improved outcomes for patients?, Crit Rev Oncol Hematol, 2017;112:153-70.

Spencer, et al. Daratumumab plus bortezomib and dexamethasone versus bortezomib and dexamethasone in relapsed or refractory multiple myeloma: updated analysis of CASTOR, Haematologica, 2018;103:2079-87.

Stewart et al., Carfilzomib, lenalidomide, and dexamethasone for relapsed multiple myeloma, N. Eng. J. Med., 372(2):142-52 (2015).

United States Food and Drug Administration. Kyprolis: Product Information. Bethesda, MD: US FDA; 2016.

Usmani et al., Carfilzomib, Dexamethasone, and Daratumumab Versus Carfilzomib and Dexamethasone for the Treatment of Patients with Relapsed or Refractory Multiple Myeloma (RRMM): Primary Analysis Results from the Randomized, Open-Label, Phase 3 Study Candor (NCT03158688), Blood, 134: 2019.

Usmani S Z. Efficacy of daratumumab in combination with standard of care regimens in lenalidomide-exposed or -refractory patients with relapsed/refractory multiple myeloma (RRMM): analysis of the castor, pollux, and MMY1001 studies, Blood, 2018;132:3288.

Usmani, et al. Clinical efficacy of daratumumab monotherapy in patients with heavily pretreated relapsed or refractory multiple myeloma, Blood, 2016;128:37-44.

Van der Veer et al., The therapeutic human CD38 antibody daratumumab improves the anti-myeloma effect of newly emerging multi-drug therapies, Blood Cancer J., 1(10):e41 (2011).

Terpos et al., Daratumumab May Attenuate Cardiac Dysfunction Related to Carfilzomib in Patients with Relapsed/Refractory Multiple Myeloma: A Prospective Study, Cancers, 13(20):5057 (2021).

Bringhen et al., Cardiovascular adverse events in modern myeloma therapy—Incidence and risks. A review from the European Myeloma Network (EMN) and Italian Society of Arterial Hypertension (SIIA), Haematologica, 103(9):1422-32 (2018).

Darzalex [package insert] p. 10, right column, Janssen Biotech (2025).

* cited by examiner

Figure 2

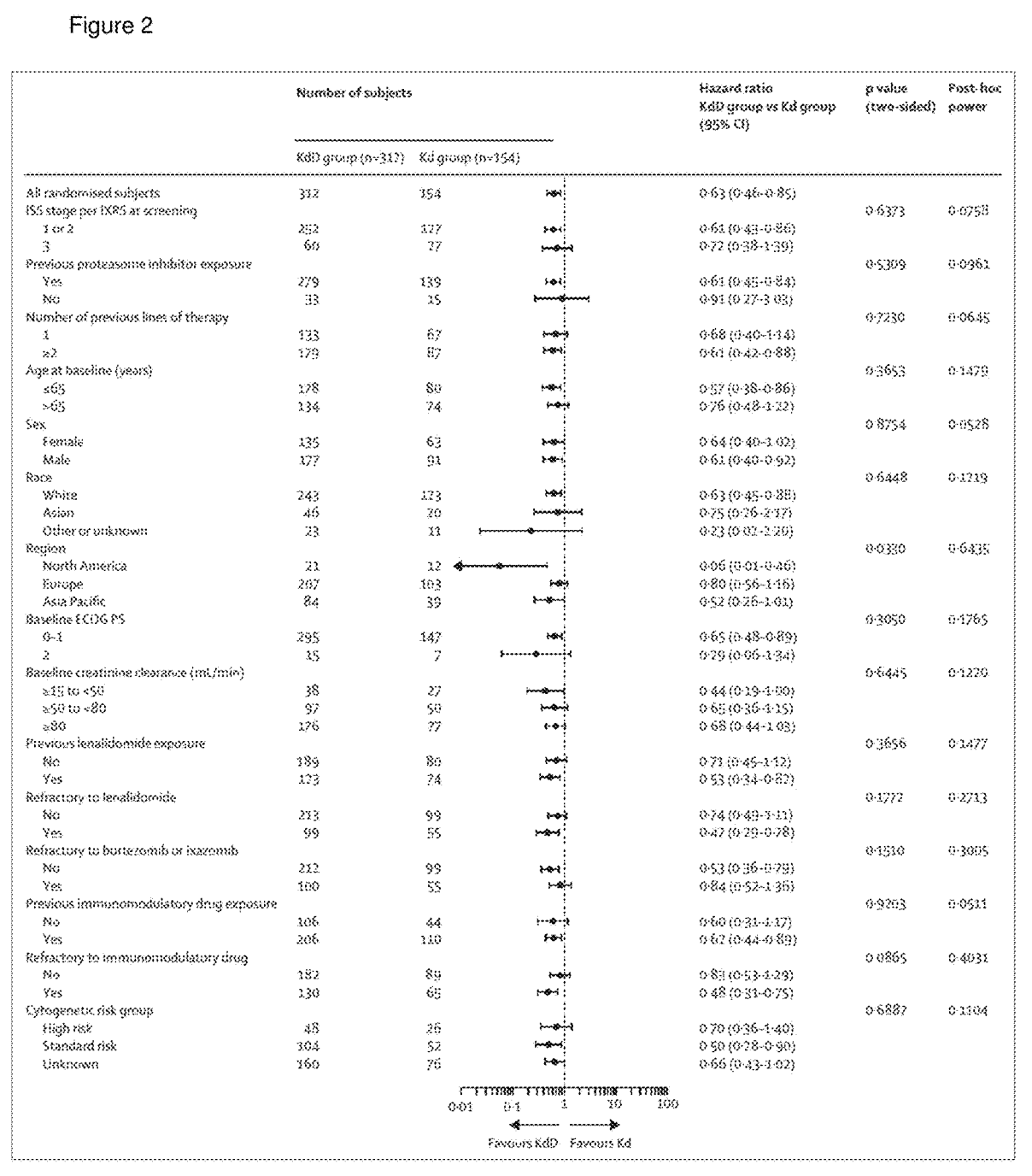

| | Number of subjects | | | Hazard ratio KdD group vs Kd group (95% CI) | p value (two-sided) | Post-hoc power |
|---|---|---|---|---|---|---|
| | KdD group (n=312) | Kd group (n=154) | | | | |
| All randomised subjects | 312 | 154 | | 0·63 (0·46-0·85) | | |
| ISS stage per IXRS at screening | | | | | 0·6373 | 0·0758 |
|   1 or 2 | 252 | 127 | | 0·61 (0·43-0·86) | | |
|   3 | 60 | 77 | | 0·72 (0·38-1·39) | | |
| Previous proteasome inhibitor exposure | | | | | 0·5309 | 0·0961 |
|   Yes | 279 | 139 | | 0·61 (0·45-0·84) | | |
|   No | 33 | 15 | | 0·91 (0·27-3·03) | | |
| Number of previous lines of therapy | | | | | 0·7230 | 0·0645 |
|   1 | 133 | 67 | | 0·68 (0·40-1·14) | | |
|   ≥2 | 179 | 87 | | 0·61 (0·42-0·88) | | |
| Age at baseline (years) | | | | | 0·3653 | 0·1479 |
|   ≤65 | 178 | 80 | | 0·57 (0·38-0·86) | | |
|   >65 | 134 | 74 | | 0·76 (0·48-1·22) | | |
| Sex | | | | | 0·8754 | 0·0528 |
|   Female | 135 | 63 | | 0·64 (0·40-1·02) | | |
|   Male | 177 | 91 | | 0·61 (0·40-0·92) | | |
| Race | | | | | 0·6448 | 0·1219 |
|   White | 243 | 123 | | 0·63 (0·45-0·88) | | |
|   Asian | 46 | 20 | | 0·75 (0·26-2·17) | | |
|   Other or unknown | 23 | 11 | | 0·23 (0·02-2·20) | | |
| Region | | | | | 0·0330 | 0·6435 |
|   North America | 21 | 12 | | 0·06 (0·01-0·46) | | |
|   Europe | 207 | 103 | | 0·80 (0·56-1·16) | | |
|   Asia Pacific | 84 | 39 | | 0·52 (0·26-1·01) | | |
| Baseline ECOG PS | | | | | 0·3050 | 0·1765 |
|   0-1 | 295 | 147 | | 0·65 (0·48-0·89) | | |
|   2 | 15 | 7 | | 0·29 (0·06-1·34) | | |
| Baseline creatinine clearance (mL/min) | | | | | 0·6445 | 0·1220 |
|   ≥15 to <50 | 38 | 27 | | 0·44 (0·19-1·00) | | |
|   ≥50 to <80 | 97 | 50 | | 0·65 (0·36-1·15) | | |
|   ≥80 | 176 | 77 | | 0·68 (0·44-1·03) | | |
| Previous lenalidomide exposure | | | | | 0·3656 | 0·1477 |
|   No | 189 | 80 | | 0·73 (0·46-1·12) | | |
|   Yes | 123 | 74 | | 0·53 (0·34-0·82) | | |
| Refractory to lenalidomide | | | | | 0·1772 | 0·2713 |
|   No | 213 | 99 | | 0·74 (0·49-1·11) | | |
|   Yes | 99 | 55 | | 0·47 (0·29-0·78) | | |
| Refractory to bortezomib or ixazomib | | | | | 0·1510 | 0·3005 |
|   No | 212 | 99 | | 0·53 (0·36-0·79) | | |
|   Yes | 100 | 55 | | 0·84 (0·52-1·36) | | |
| Previous immunomodulatory drug exposure | | | | | 0·9263 | 0·0511 |
|   No | 106 | 44 | | 0·60 (0·31-1·17) | | |
|   Yes | 206 | 110 | | 0·62 (0·44-0·89) | | |
| Refractory to immunomodulatory drug | | | | | 0·0865 | 0·4031 |
|   No | 182 | 89 | | 0·83 (0·53-1·29) | | |
|   Yes | 130 | 65 | | 0·48 (0·31-0·75) | | |
| Cytogenetic risk group | | | | | 0·6887 | 0·1304 |
|   High risk | 48 | 26 | | 0·70 (0·36-1·40) | | |
|   Standard risk | 104 | 52 | | 0·50 (0·28-0·90) | | |
|   Unknown | 160 | 76 | | 0·66 (0·43-1·02) | | |

0·01　0·1　1　10　100

← Favours KdD　　Favours Kd →

US 12,636,340 B2

| 1 | 2 |

METHODS OF TREATING MULTIPLE MYELOMA

BACKGROUND

The availability of novel agents has increased survival for multiple myeloma (MM) patients.[1-3] Despite therapeutic advances, relapse is inevitable, and myeloma remains largely incurable.[4,5] Prolonged lenalidomide-based treatment has become standard frontline therapy.[6-9] With exposure of many newly diagnosed MM patients to bortezomib or lenalidomide, resistance to these agents develops.[10,11] Moreover, lenalidomide intolerance may ensue with long-term lenalidomide maintenance therapy.[11] There is a need to define active and tolerable therapeutic options for relapsed or refractory MM.

INCORPORATION BY REFERENCE OF MATERIALS SUBMITTED ELECTRONICALLY

The application contains, as a separate part of the disclosure, a Sequence Listing in computer readable form, Filename: 40006_Seqlisting.txt; Size: 8,340 bytes; Created: Apr. 28, 2021, which is incorporated by reference in its entirety.

SUMMARY

Provided herein are methods of treating multiple myeloma in a subject suffering therefrom comprising administering to the subject a therapeutically effective amount of a triplet therapy of (a) carfilzomib; (b) an antibody that specifically recognizes CD38; and (c) dexamethasone. In some cases, the subject has been on 1 to 3 previous lines of treatment for multiple myeloma, has previously been on a lenalidomide treatment (e.g., lenalidomide-exposed or lenalidomide-refractory), or has previously been on a bortezomib treatment. In various cases, the subject exhibits longer progression-free survival, compared to a subject on a doublet therapy of carfilzomib and dexamethasone alone. In various cases, the subject exhibits higher minimal residual disease (MRD) negative-complete response rate, compared to a subject on a doublet therapy of carfilzomib and dexamethasone alone, e.g., at least 5 times higher than that of the subject on the doublet therapy. In some cases, the subject exhibits a lower risk of progression or death, compared to a subject on a doublet therapy of carfilzomib and dexamethasone alone.

In various cases, the triplet therapy is administered in cycles of 4 weeks. In some cases, carfilzomib is administered on day 1 and day 2 of a first cycle at a dose of 20 mg/m², then at a twice weekly dose of 56 mg/m² for week 2 and week 3 with a one week dosing holiday, and at a twice weekly dose of 56 mg/m² for three weeks and a one week dosing holiday during subsequent cycles. In some cases, the antibody that specifically recognizes CD38 is daratumumab. In various cases, the antibody that specifically recognizes CD38 is administered according to a dosing regimen of: (i) a dose of 8 mg/kg on day 1 and day 2 of week 1 of a first 4-week cycle, (ii) a dose of 16 mg/kg once weekly for weeks 2, 3, and 4 of the first 4-week cycle, (iii) a dose of 16 mg/kg once weekly for all doses of a second 4-week cycle, (iv) a dose of 16 mg/kg once every two weeks for all doses for 4-week cycles 3, 4, 5, and 6, and (v) a dose of 16 mg/kg once every four weeks for each 4-week cycle thereafter. In various cases, the dexamethasone is administered at a dose of 20 mg weekly. In some cases, the dexamethasone is administered at a dose of 40 mg weekly, and in some specific cases, in two divided doses of 20 mg each.

BRIEF DESCRIPTION OF THE FIGURES

FIG. 2 shows a chart of the assessment of a carfilzomib-dexamethasone-daratumumab therapy (KdD) therapy compared to a carfilzomib-dexamethasone therapy (Kd) for various types of subjects (e.g., prior number of lines of therapy, age, race, sex, region, etc.).

DETAILED DESCRIPTION

Figure 1:
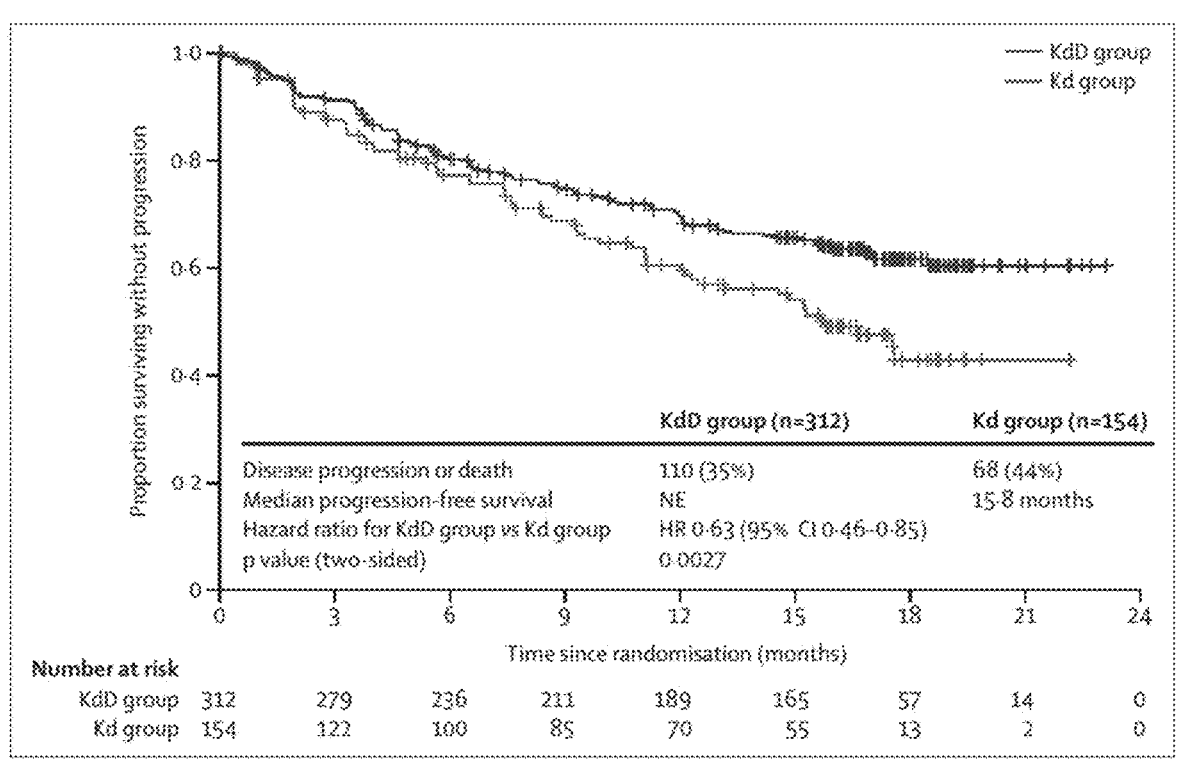
FIG. 1 shows progression of disease for subjects treated with a carfilzomib-dexamethasone-daratumumab therapy (KdD) compared to that of subject treated with a carfilzomib-dexamethasone therapy (Kd).

Provided herein are methods for treating multiple myeloma (MM) in a subject suffering therefrom, in some cases, subject who are refractory or relapsed, comprising administering a triplet therapy of carfilzomib, dexamethasone, and an antibody that specifically recognizes CD38. In embodiments, the disclosed methods result in significantly longer progression-free survival and/or deeper responses, with nearly 10 times higher minimal residual disease negative-complete response rate, compared to subjects treated with a doublet therapy of carfilzomib and dexamethasone.

Carfilzomib is a selective proteasome inhibitor that irreversibly binds the proteasome, eliciting anti-myeloma activity through unfolded protein stress response and other mechanisms.[12] Carfilzomib is approved for single-agent use, or as part of doublet (with dexamethasone) or triplet combination (with dexamethasone and lenalidomide) regimens for relapsed and/or refractory MM.[3,13-18] In the methods disclosed herein, carfilzomib can be administered as an infusion.

The anti-CD38 monoclonal antibody daratumumab exerts anti-myeloma effects through immune-mediated, direct on-tumor and immunoregulatory actions.[19] Daratumumab has been combined with standards of care, including proteasome inhibitors, for treatment of relapsed or refractory MM,[20-22] and is approved for treatment of newly diagnosed and relapsed or refractory MM patients.[23] The term "CD38" as used herein refers to cluster of differentiation 38 protein, a glycoprotein expressed on immune cells, including plasma cells, natural killer cells and subpopulations of B and T cells. In some embodiments, the malignant plasma cells of the multiple myeloma express CD38. An antibody that "specifically recognizes CD38" as used herein refers to an antibody or fragment thereof that immunospecifically binds to CD38.

The term "antibody" includes immunoglobulin molecules including monoclonal antibodies including human, humanized and chimeric monoclonal antibodies. Full-length antibody molecules are comprised of two heavy chains (HC) and two light chains (LC) inter-connected by disulfide bonds. Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL regions may be further subdivided into regions of hypervariability, termed complementarity determining regions (CDRs), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

In some embodiments, the antibody that specifically recognizes CD38 comprises the HCDR1, HCDR2, and HCDR3 as set forth in the amino acid sequence of SEQ ID NO: 1 and the LCDR1, LCDR2, and LCDR3 as set forth in the amino acid sequence of SEQ ID NO: 2. In some embodiments, the antibody that specifically recognizes CD38 comprises the VH of SEQ ID NO: 1 and the VL of SEQ ID NO: 2. In some embodiments, the antibody that specifically recognizes CD38 comprises the heavy chain (HC) of SEQ ID NO: 3 and the light chain (LC) of SEQ ID NO: 4. In some embodiments, the antibody that specifically recognizes CD38 is daratumumab.

The clinical benefit of combining daratumumab with proteasome inhibition was confirmed in the phase 3 CASTOR study where patients received up to 8 cycles of bortezomib and dexamethasone and showed improved outcomes with daratumumab-bortezomib-dexamethasone versus bortezomib-dexamethasone.[22] Carfilzomib (56 mg/m$^2$ twice-weekly) has demonstrated superior efficacy over bortezomib in the randomized phase 3 ENDEAVOR trial.[17] Compelling efficacy and safety of combining daratumumab with carfilzomib (70 mg/m$^2$ once-weekly)-dexamethasone was initially demonstrated in the nonrandomized phase 1 b MMY1001 study in relapsed or refractory MM.[24] Herein is provided methods of administering a triplet therapy of carfilzomib-dexamethasone-daratumumab (KdD) in, e.g., relapsed or refractory MM patients, and compared to efficacy and safety of a doublet therapy of carfilzomib-dexamethasone (Kd) alone.

As used herein, a subject who has "relapsed" multiple myeloma refers to a subject who has been on a therapy to treat multiple myeloma, but the cancer has returned after the therapy or after a period of remission. "Refractory" multiple myeloma is when a subject is initially responds to a particular therapy to treat multiple myeloma but then becomes resistant or exhibits worsening response to that therapy. The term "newly diagnosed" as used herein refers to a subject who has been diagnosed with but has not yet received a treatment for multiple myeloma.

For the methods disclosed herein, subjects can be ones who have been previously treated with 1 to 3 (or greater) lines of therapy. A line of therapy is defined as one or more cycles of a planned treatment program, which may be one or more planned cycles of single-agent therapy or a combination therapy, or a sequence of treatments administered in a planned manner. A new line of therapy begins when a planned course of therapy is modified to include other treatment agents due to lack of adequate response, disease progression (even if the level of progression did not yet meet International Myeloma Working Group Uniform Response Criteria—"IMWG-URC"—criteria for progressive disease), relapse, or toxicity. Previous lines of treatment include, but are not limited to, therapy comprising carfilzomib, bortezomib, lenalidomide, a CD38 antibody therapy, stem cell transplant, or any combination thereof. In some cases, the subject had previously been administered bortezomib either alone or in combination with other multiple myeloma treatments (e.g., dexamethasone, a CD38 antibody therapy).

In some cases, the subject is lenalidomide-exposed or lenalidomide-refractory. Lenalidomide-exposed means that at least one of the subject's previous lines of therapy included lenalidomide. A subject is lenalidomide refractory when their disease was nonresponsive while on a lenalidomide-containing primary or salvage therapy or their disease had progressed within 60 days of the last date of cessation of lenalidomide treatment.

The term "progression-free survival (PFS)" means time from initiation of therapy to first evidence of disease progression or death due to any cause, whichever occurs first. For the purpose of the clinical trial described in the example, PFS is defined as the time from randomization of study population to the first documented progressive disease or death due to any cause. In some embodiments, administration of carfilzomib and dexamethasone with an antibody that specifically recognizes CD38 provides an increase in the progression-free survival of a human subject with multiple myeloma, compared to a human subject who is administered carfilzomib and dexamethasone alone. The increase in the progression-free survival refers to an increase in PFS in multiple myeloma (MM) patients treated with carfilzomib, dexamethasone, and daratumumab relative to PFS in MM patients treated with carfilzomib and dexamethasone only. In some embodiments, the increase in progression-free survival is about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months, about 25 months, about 26 months, about 27 months, about 28 months, about 29 months, about 30 months, about 31 months, about 32 months, about 33 months, about 34 months, about 35 months, about 36 months, or greater than 36 months increased over that of a subject administered the doublet therapy of carfilzomib-dexamethasone alone.

The terms "partial response" (PR), "very good partial response" (VGPR), "complete response" (CR), "stringent complete response" (sCR), as used herein take their customary meanings as will be understood by a person skilled in the art of designing, conducting, or reviewing clinical trials. International Uniform Response Criterial Consensus Recommendations can be used to assess response. The term "overall response rate" (ORR) as used herein amounts to the sum of the rates of PR+VGPR+CR+sCR.

The term "Minimal residual disease (MRD)" as used herein refers to a small number of multiple myeloma cells that remain in the patient after treatment and/or during remission. "MRD negative" refers to a ratio of 1:10×10$^5$ or less clonal multiple myeloma cells in a bone marrow aspirate sample from the subject. In some embodiments, the MRD negative rate is at least 1.5 times higher, at least 2 times higher, at least 3 times higher, at least four times higher, at least five times higher, at least 6 times higher, at least 7 times higher, at least 8 times higher, at least 9 times higher, at least 10 times higher, or up to 5 times higher, up to 6 times higher, up to 7 times higher, up to 8 times higher, up to 9 times higher, up to 10 times higher, up to 11 times higher, or up to 15 times higher than the MRD negative rate of a subject administered the doublet therapy of carfilzomib-dexamethasone alone.

MRD negative-complete response rate as used herein refers to the MRD negative assessment of a subject that has also achieved a complete response or better (a MRD negative-complete response rate). In some cases, the MRD negative-complete response rate is at least 1.5 times higher, at least 2 times higher, at least 3 times higher, at least four times higher, at least five times higher, at least 6 times higher, at least 7 times higher, at least 8 times higher, at least 9 times higher, at least 10 times higher, or up to 5 times higher, up to 6 times higher, up to 7 times higher, up to 8 times higher, up to 9 times higher, up to 10 times higher, up to 11 times higher, or up to 15 times higher than the MRD negative-complete response rate of a subject administered the doublet therapy of carfilzomib-dexamethasone alone.

The term "risk of progression" or "death" as used herein take their customary meanings as will be understood by a person skilled in the art of designing, conducting, or reviewing clinical trials. International Uniform Response Criterial Consensus Recommendations can be used to assess these terms.

The terms "co-administration," "administration with," "administration in combination with," or the like, as used herein, encompass administration of the selected therapeutic agents to a single patient, and are intended to include treatment regimens in which the agents are administered by the same or different route of administration or at the same or different time.

The disclosed triplet therapy can be performed in cycles of 4 weeks. In the first four weeks of the triplet therapy (cycle 1), a subject can be administered the three drugs in the following manner: carfilzomib at day 1 and day 2 during week 1, then twice weekly for weeks 2 and 3, then not at all on week 4 (i.e., a dosing holiday of 1 week), the antibody that specifically recognizes CD38 (e.g., daratumumab) at day 1 and day 2, and dexamethasone once weekly for each of weeks 1, 2, 3, and 4. In some cases, the dose of carfilzomib is 20 mg/m$^2$ for each dose given during week 1 of cycle 1; and the dose of carfilzomib is 56 mg/m$^2$ for each dose given during weeks 2 and 3 of cycle 1. In some cases, the dose of daratumumab is 8 mg/kg for each dose given during week 1 of cycle 1, and the dose of daratumumab is 16 mg/kg for each dose given during weeks 2, 3 and 4 of cycle 1. Dexamethasone is administered at a weekly dose of 20 mg or 40 mg for each week of cycle 1 either intravenously or orally. In some cases, the dexamethasone is administered at a weekly dose of 40 mg and given in two divided doses of 20 mg per day on two subsequent days of any particular week of cycle 1.

For the second four week cycle (cycle 2), a subject can be administered the three drugs in the following manner: carfilzomib twice weekly during weeks 1, 2, and 3 of cycle 2 and a dosing holiday during week 4 of cycle 2; the antibody that specifically recognizes CD38 (e.g., daratumumab) once per week for each of weeks 1, 2, 3, and 4; and dexamethasone once weekly for each of weeks 1, 2, 3, and 4. In some cases, the dose of carfilzomib is 56 mg/m$^2$ for each dose given during cycle 2. In some cases, the dose of the antibody that specifically recognizes CD38 is 16 mg/kg for each dose given during cycle 2. Dexamethasone is administered at a weekly dose of 20 mg or 40 mg for each week of cycle 2 either intravenously or orally. In some cases, the dexamethasone is administered at a weekly dose of 40 mg and given in two divided doses of 20 mg per day on two subsequent days of any particular week of cycle 2.

For the third, fourth, fifth, and sixth four week cycle (cycles 3, 4, 5 and 6), a subject can be administered the three drugs in the following manner: carfilzomib twice weekly during weeks 1, 2, and 3 of each cycle and a dosing holiday during week 4 of the cycle; the antibody that specifically recognizes CD38 (e.g., daratumumab) once every other week (i.e., week 1 and 3, or week 2 and 4); and dexamethasone once weekly for each of weeks 1, 2, 3, and 4 of the cycle. In some cases, the dose of carfilzomib is 56 mg/m$^2$ for each dose given during each of cycles 3, 4, 5, and 6. In some cases, the dose of the antibody that specifically recognizes CD38 is 16 mg/kg for each dose given during cycles 3, 4, 5, and 6. Dexamethasone is administered at a weekly dose of 20 mg or 40 mg for each week of each cycle either intravenously or orally. In some cases, the dexamethasone is administered at a weekly dose of 40 mg and given in two divided doses of 20 mg per day on two subsequent days of any particular week of the cycle.

For subsequent cycles (e.g., cycles 7+), a subject can be administered the three drugs in the following manner: carfilzomib twice weekly during weeks 1, 2, and 3 of each cycle and a dosing holiday during week 4 of the cycle; the antibody that specifically recognizes CD38 (e.g., daratumumab) once every 4 weeks (e.g., once during week 1, or once during week 2, or once during week 3, or once during week 4 only); and dexamethasone once weekly for each of weeks 1, 2, 3, and 4 of the cycle. In some cases, the dose of carfilzomib is 56 mg/m$^2$ for each dose given during each subsequent cycle. In some cases, the dose of the antibody that specifically recognizes CD38 is 16 mg/kg for the single dose given during each subsequent cycle. Dexamethasone is administered at a weekly dose of 20 mg or 40 mg for each week of each subsequent cycle either intravenously or orally. In some cases, the dexamethasone is administered at a weekly dose of 40 mg and given in two divided doses of 20 mg per day on two subsequent days of any particular week of the cycle.

As used herein, a "dosing holiday" refers to a period of time where a particular drug is not given. For example, in a four week cycle, the carfilzomib is administered at various timings and doses for three of the four weeks, and for one week no carfilzomib is administered—that one week with no carfilzomib administered is considered a dosing holiday of the carfilzomib.

DISCUSSION

The clinical benefit of combining a CD38-targeting antibody with proteasome inhibition was first confirmed in the phase 3 CASTOR study.[22] The CASTOR study demonstrated a 61% decreased risk in progression or death when daratumumab was combined with bortezomib and dexamethasone (DVd) versus bortezomib and dexamethasone alone. Notably, in CASTOR, bortezomib was administered for a fixed duration of 8 cycles in both arms, while daratumumab was given until disease progression in the experimental arm only. The CANDOR study demonstrates that a second-generation proteasome inhibitor can be combined with daratumumab and administered until disease progression. Moreover, Kd has demonstrated superior efficacy over bortezomib and dexamethasone.[17]

The results from this large phase 3 study show that KdD significantly prolonged PFS and reduced the risk of progression or death by 37% compared with Kd among relapsed or refractory MM patients. Consistent with outcomes in the overall population, the risk of progression or death was reduced with KdD versus Kd across pre-specified subgroups. In addition, most patients (90%) in the CANDOR study were previously treated with bortezomib-containing regimens, reflecting the current MM treatment landscape. KdD demonstrated a clinical benefit over Kd by reducing the risk of progression or death by 36% for patients with previous proteasome inhibitor exposure, including bortezomib. The risk of progression or death was also reduced with KdD among CANDOR patients with high or standard risk cytogenetic status. While the HR for progression-free survival is intriguing for patients from North America (HR=0.056), the Gail and Simon qualitative test did not show any significance. Hence, this finding should be interpreted with caution as it may largely be associated with the small sample size.

Deep responses, including MRD negativity, have been associated with longer PFS and overall survival in newly diagnosed and relapsed or refractory MM.[2,27,28] In this study, patients were assessed for MRD negative-complete response per IMWG uniform response criteria. KdD-treated patients had a statistically significantly higher overall response rate and achieved deeper responses, with a nearly 10-times higher rate of achieving MRD negative-complete response at 12 months compared with Kd-treated patients. Best MRD negative-complete response rates were also higher for KdD compared with Kd (13.8% vs. 3.2%).

The prolonged PFS and deep responses achieved with KdD in the CANDOR study are consistent with findings from a study of daratumumab with once-weekly carfilzomib at 70 mg/m$^2$ and dexamethasone in patients nearly entirely pre-exposed to lenalidomide and 60% lenalidomide-refractory, and reinforce the efficacy of KdD for treatment of relapsed or refractory MM.[24] In that study (the MMY1001 study), median PFS was not reached for KdD in the overall population and was 257 months for lenalidomide-refractory patients. Overall response rate was 84%; complete response rate was 33%.

At a median follow up of nearly 17 months, overall survival was not yet mature; however, fewer deaths occurred in the KdD arm (18.9%) versus the Kd arm (23.4%) and a trend towards an overall survival benefit for KdD versus Kd was observed.

While KdD was associated with higher rates of any-grade, grade 3 or higher, and fatal AEs versus Kd, treatment duration was almost 2 times longer in the KdD group than the Kd group. The incidence of AEs leading to treatment discontinuation was similar in both treatment groups (22.4% vs. 24.8%). Exposure adjustment attenuated the observed difference in AE rates between the KdD and Kd groups. The risk estimates for grade 3 or higher and serious AEs were similar in the treatment groups after exposure adjustment.

Grade 3 or higher respiratory tract infections (grouped term) were AEs of interest that occurred more frequently with KdD (KdD, 28.9%; Kd, 15.7%) and are consistent with higher incidences of respiratory infections observed in the daratumumab arm of the CASTOR study.[22] Aggressive monitoring and timely management of infections would be appropriate for patients deemed at high risk for complications.

Grade 3 or higher cardiac failure (grouped term: KdD, 3.9%; Kd, 8.5%) and acute renal failure (grouped term: 2.9% and 6.5%) rates were lower in the KdD group versus the Kd group. The rate of cardiac failure events leading to carfilzomib treatment discontinuation was similar in the KdD and Kd group (2.0% and 1.9%) while the rate of renal events leading to carfilzomib treatment discontinuation was lower in the KdD group (0.6% and 3.9%). No new cardiovascular safety risks were identified with the addition of daratumumab to carfilzomib-dexamethasone.

Most treatment-related fatal AEs were the result of infections. Upon evaluation of baseline patient characteristics, we found a higher frequency of treatment-emergent fatal AEs in the KdD than Kd group (KdD, 13.7%; Kd, 2.6%) in the older patient population (age 65 years) relative to younger patients <65 years (KdD, 6.2%; Kd, 7.8%). Furthermore, a higher proportion of patients in the KdD group who were classified by the investigator as intermediate fit had fatal AEs compared with the Kd group (18.9% vs. 2.9%). Neutropenia was not associated with the higher rates of infection-related fatal AEs in the KdD arm. Infections were observed after 12 weeks in the population of relapsed/refractory MM patients studied in CANDOR. Although treatment with prophylactic levofloxacin during the first 12 weeks of myeloma therapy has been shown to reduce the incidence of infections and death in newly diagnosed multiple myeloma patients (TEAMM study)[29], the applicability of prophylactic levofloxacin treatment in the setting of CANDOR (i.e., a KdD therapy) is still being investigated. These results suggest that close monitoring and management of infections are important when administering KdD to older and/or less fit patients.

With increased use of frontline lenalidomide therapy, there is a rising need for new, tolerable and efficacious lenalidomide-free regimens for patients who have been exposed to or have relapsed after stopping lenalidomide treatment. The results for KdD were generally consistent across prespecified subgroups, including lenalidomide-exposed and lenalidomide-refractory. The observation of a median PFS not reached after 17 months of follow-up for KdD compares favorably with the median PFS range of 7.8 months to 11.2 months reported for other lenalidomide-free regimens in lenalidomide-exposed or -refractory populations.[10,26,30,31]

In summary, KdD resulted in a significant PFS benefit compared with Kd. In addition, patients treated with KdD achieved improved overall responses and deeper responses, with a nearly 10 times higher MRD negative-complete response rate at 12 months. The treatment effect on PFS was generally consistent across prespecified clinically important subgroups, including lenalidomide-exposed and -refractory subgroups. The observed AEs associated with KdD were consistent with the known safety profiles of each agent, suggesting that combining daratumumab with carfilzomib does not result in additional toxicity. Carfilzomib treatment discontinuations and dose reductions were comparable between the KdD and Kd groups, and AEs were generally tolerable and manageable. Overall, the immunomodulatory drug-free KdD regimen showed a favorable benefit-risk profile and represents an efficacious new standard of care for patients with relapsed or refractory MM, including patients for whom lenalidomide is no longer a treatment option.

EXAMPLES

CANDOR was a phase 3, randomized, open-label, multicenter trial comparing carfilzomib/dexamethasone/daratumumab (KdD) versus carfilzomib/dexamethasone (Kd) in patients with relapsed or refractory multiple myeloma (MM) patients. Key eligibility criteria for inclusion in this trial included relapsed or refractory MM patients with measurable disease who received 1 to 3 previous treatment lines with partial response or better to at least 1 prior therapy line; left ventricular ejection fraction ≥40%; absolute neutrophil count (ANC)≥1×10$^9$/L within 21 days prior to randomization; platelet count ≥75×10$^9$/L (≥50×10$^9$/L if myeloma involvement in the bone marrow was ≥50%) within 21 days prior to randomization; and calculated or measured creatinine clearance (CrCl) of ≥20 mL/min within 21 days prior to randomization. Key exclusion criteria related to significant baseline pulmonary and cardiac disease, including uncontrolled hypertension (defined as an average systolic blood pressure >159 mmHg or diastolic >99 mmHg despite optimal treatment). Analysis of LVEF changes over time was conducted. Long-term corticosteroid treatment equivalent to a dexamethasone dose of 4.0 mg/day or prednisone at a dose of >20 mg/day was not permitted while receiving study treatment. Corticosteroids administered short-term (up to 2 weeks) were permitted, provided the cumulative dose was less than a 40 mg per week dexamethasone equivalent.

Patients were randomized 2:1 to receive carfilzomib with dexamethasone and daratumumab (KdD group) or carfilzomib and dexamethasone alone (Kd) in 28-day cycles until disease progression. Randomization was performed using an interactive voice or web response system. Patients were stratified by international Staging System at screening (Stage 1 or 2 vs Stage 3), previous proteasome inhibitor exposure (yes vs. no), number of previous lines of therapy (1 vs ≥2), and prior CD38 antibody therapy (yes vs. no). In each stratum defined by the stratification factors, patients were randomly assigned to treatment based on a blocked randomization scheme (block size of 6).

All patients received carfilzomib as a 30-min intravenous infusion on days 1, 2, 8, 9, 15, and 16 of each 28-day cycle (20 mg/m$^2$ on days 1 and 2 during cycle 1 and 56 mg/m$^2$ thereafter). Daratumumab (8 mg per kilogram) was administered as an intravenous infusion on days 1 and 2 of cycle 1 and at 16 mg per kilogram once weekly for the remaining doses of the first 2 cycles, then every 2 weeks for 4 cycles (cycles 3 to 6), and every 4 weeks thereafter. Dexamethasone was administered orally or by intravenous infusion at 40 mg weekly or 20 mg weekly for patients older than 75 years of age. A split dose of dexamethasone at 20 mg each day was administered when taken on successive days.

Disease assessments were made per International Myeloma Working Group Uniform Response Criteria (IMWG-URC),[25] using central laboratory test results obtained every 28±7 days until confirmed disease progression. After disease progression or treatment discontinuation, patients had 2 follow-up visits, and then were followed for survival every 3 months. MRD negative-complete response was defined according to the 2016 IMWG-URC[25] and assessed in the bone marrow by next generation sequencing at a threshold of 1 tumor cell per 10$^{-5}$ white cells at a fixed landmark of 12 months (±4 weeks).

The primary endpoint was progression-free survival (PFS). Secondary endpoints included overall response rate, minimal residual disease (MRD) negative-complete response rate at 12 months, overall survival, time to response, and safety. PFS was assessed as time from randomization until disease progression of death from any cause, whichever occurs first. Overall response rate was assessed as the proportion of best overall response of sCR, CR, VGPR, and PR by committee assessment. MRD-negative CR rated was assessed as achievement of CR (includes sCR) per the IMWG-URC criteria and MRD-negative status as assessed by next generation sequencing (at a 10$^{-5}$ level). Time to response was assessed as the time from randomization to the earliest date a response of PR or better is first achieved and subsequently confirmed for subjects with a best response of PR or better. Duration of response was assessed as the time from first evidence of PR or better, as defined by IMEG-URC criteria, to the earliest of disease progression or death due to any cause for subjects with a best response of PR or better. Overall survival was assessed as the time from randomization until death for any cause.

Statistical analysis: Efficacy evaluations were based on the intention-to-treat population. Safety analyses included all patients with at least 1 study treatment dose. For primary and key secondary endpoints, response and disease progression were determined by a blinded Independent Review Committee. Additionally, they were determined locally by investigators in an unblinded manner and centrally by the sponsor using a validated computer algorithm, which served as sensitivity analysis of PFS. Sample size was determined such that a total of 188 disease progression or death events provided at least 90% power to demonstrate superiority at an alternate hazard ratio of 0.6 (KdD group vs. Kd group), using a log-rank test at a two-sided overall significance level of 0.05.

Hierarchical sequential testing adjusted for multiplicity: if PFS was met, key secondary endpoints were sequentially tested in the order of overall response rate, MRD negative-complete response rate, and overall survival. Comparisons of PFS and overall survival between groups was done using a stratified log-rank test. Hazard ratios were estimated using a stratified Cox proportional-hazards model. Kaplan-Meier methodology was used to summarize distributions. The adequacy of the proportional hazard assumption for Cox regression models was assessed using the plot of the logarithm of the estimated hazard functions based on the Kaplan-Meier method against the logarithm of time-to-event endpoints, as well as the plot of the scaled Schoenfeld residuals by time. Based on a visual interpretation, no major violation on proportional hazard assumption was observed.

Overall response rate and MRD negative-complete response rate were compared between groups using Cochran-Mantel-Haenszel chi-square methods. Odds ratios and corresponding 95% confidence intervals (CI) were estimated using Mantel-Haenszel methods. These analyses were stratified using randomization strata.

In addition, the primary endpoint was analyzed within prespecified subgroups according to age, sex, race, geographical region, baseline organ function, and baseline disease characteristics. To evaluate the subgroup effects, the adjusted hazard ratio with the corresponding 95% confidence interval were presented using the stratified Cox proportional hazard model with the stratification factors (as assessed at randomization) including: International Staging System (ISS) stage (Stage 1 or 2 vs Stage 3) at screening; prior proteasome inhibitor exposure (yes vs no); number of prior lines of therapy (1 vs 2). The treatment effect was also evaluated using Gail and Simon (GS) quantitative interaction tests (1985) based on the same stratified Cox proportional hazard model. Post hoc power for a nominal 2-sided 5% significance level test are calculated to help aid in the assessment.

Descriptive statistics identified the extent of missing data. Incomplete adverse event start dates, concomitant medications start or stop dates, and death date were imputed. For patients who died on study, the death date was recorded on the end of study CRF page at the end of the study date. If only the day of death date was missing, death date was imputed using the following rules: 1) Day 1 of the month was used to impute if year and month indicate that death happened later than last known alive date; 2) One day after last known alive date was used to impute if death happened in the same month and year as last known alive date. The imputed death date was used in calculation of duration of response, progression-free survival and overall survival.

Results 466 patients were randomized to either KdD (n=312) or Kd. (n=154). Four of the 312 patients in the KdD group did not receive allocated treatment (adverse event [n=1], sponsor's decision [n=2], death [n=1]). One of the 154 patients in the Kd group did not receive treatment (sponsor's decision [n=1]). Except for a higher proportion of patients with a previous stem cell transplant in the KdD group compared with the Kd group (195 [62.5%] of 312 vs 75 [48.7%] of 154) and a higher proportion of patients 75 years of age in the Kd group (KdD, 28 [9.0%]); Kd, 22 [14.3%]), baseline characteristics were generally balanced between treatment groups.

Of 466 randomized patients, 197 (42.3%) received previous lenalidomide-containing regimens; 421 (90.3%) received previous bortezomib-containing regimens. 154 (33.0%) were lenalidomide-refractory; 135 (29.0%) were bortezomib-refractory.

After at least a year of treatment (starting study between June 2017 and June 2018, and assessed as of July 2019), 233 patients in the KdD group (74.7%) and 107 in the Kd group (69.5%) continued in the study. 178 (38.2%) of 466 patients had PFS events (110 [35.3%] of 312 events in the KdD group; 68 [44.2%] of 154 events in the Kd group) were assessed by the data cutoff. Of the randomized patients, 286 patients (179 [57.4%] of 312 in the KdD group; 107 [69.5%] of 154 in the Kd group] discontinued carfilzomib due to AEs (KdD, n=52 [16.7%]; Kd, n=28 [18.2%]), disease progression (KdD, n=80 [25.6%]; Kd, n=60 [39.0%]), and other factors (KdD, n=47 [15.1%]; Kd, n=19 [12.3%]. 151 (48.4%) of 312 patients discontinued daratumumab in the KdD group due to AEs (n=18 [5.8%]), disease progression, (n=88 [28.2%]) and other factors (n=45 [14.4%]). 269 patients (161 [51.6%] of 312 in the KdD group; 108 [70.1%] of 154 in the Kd group]) discontinued dexamethasone due to AEs (KdD, n=23 [7.4%]; Kd, n=31 [20.1%]), disease progression (KdD, n=85 [27.2%]; Kd, n=58 [37.7%]), and other factors (KdD group, n=53 [17.0%]; Kd group, n=19 [12.4%]). The primary endpoint of PFS was met. Median follow-up time for PFS was 16.9 months (95% CI, 16.7-17.5; IQR, 15.9-18.6) and 16.3 months (95% CI, 15.9-16.7; IQR, 12.1-17.6) in the KdD and Kd groups, respectively. The hazard ratio for progression or death in the KdD group versus the Kd group was 0.630 (95% CI, 0.464-0.854; 2-sided P=0.0027). Median PFS was not reached in the KdD group (95% CI, not estimable) versus 15.8 months (95% CI, 12.1 to not estimable) in the Kd group. The Kaplan-Meier 18-month PFS rates were 61.5% (95% CI, 55.4-67.1) in the KdD group and 42.8% (95% CI, 32.4-52.8) in the Kd group. Median time to progression was not reached (95% CI, not estimable) and 17.5 months (95% CI, 13.2 to not estimable) in the KdD and Kd groups, respectively.

PFS benefit was generally consistent across pre-specified subgroups of clinical relevance. Median PFS was not reached (95% CI, 18.5 to not estimable) in the KdD group versus 12.1 months (95% CI, 8.4-15.3) in the Kd group for patients who had prior exposure to lenalidomide (hazard ratio, 0.529; 95% CI, 0.342-0.818). Similarly, median PFS was not reached (95% CI, 18.5 to not estimable) in the KdD group versus 11.1 months (95% CI, 7.4-14.9) in the Kd group for patients who were lenalidomide-refractory at any prior line of treatment (hazard ratio, 0.474; 95% CI, 0.288-0.781). Median PFS was not reached in either treatment group (95% CI for KdD, not estimable; 95% CI for Kd, 15.8 to not estimable) for patients who had no prior exposure to lenalidomide (hazard ratio, 0.708; 95% CI, 0.448-1.120). Median PFS was also not reached in either treatment group (95% CI for KdD, not estimable; 95% CI for Kd, 15.7 to not estimable) for patients who were not refractory to lenalidomide (hazard ratio, 0.738; 95% CI, 0.492-1.108).

Overall response rates were achieved by 263 (84.3%; 95% CI, 79.8-88.1) of 312 in the KdD group and 115 (74.7%; 95% CI, 67.0-81.3) of 154 in the Kd group (odds ratio, 1.925; P=0.0080), with 216 (69.2%) and 75 (48.7%) patients in the two groups respectively achieving very good partial response or better, and 89 (28.5%) and 16 (10.4%) of patients in the two groups, respectively, achieving complete response. Median time to first response was 1 month in both treatment groups; median time to complete response was 8.4 and 7.0 months for KdD and Kd groups, respectively. The MRD-negative rate at 12 months was achieved by 55 (17.6%; 95% CI, 13.6-22.3) of 312 patients for the KdD group and 6 (3.9%; 1.4-8.3) of 154 patients for the Kd group (odds ratio, 5.762; 95% CI, 2.375-13.979; P<0.0001). The proportion of randomized patients achieving a complete response per IMWG response criteria and MRD-negative status at any time during the study was 43 (13.8%) in the KdD group and 5 (3.2%) in the Kd group. MRD negative-complete response rates at 12 months were achieved by 39 patients (12.5%; 95% CI, 9.0-16.7) in the KdD group versus 2 patients (1.3%; 95% CI, 0.2-4.6) in the Kd group (odds ratio, 11.329; 95% CI, 2.703-47.476; P<0.0001).

At a median follow-up time of 17.2 months (KdD group; IQR, 16.3-18.7) and 17.1 months (Kd group; IQR, 16.2-18.7), median overall survival was not reached in either treatment group (hazard ratio for death, 0.745; 95% CI, 0.491-1.131, P=0.1672). A total of 95 deaths had occurred by the data cutoff date, with 59 (18.9%) and 36 (23.4%) deaths reported in the KdD and Kd groups, respectively. The Kaplan-Meier 18-month overall survival rates were 79.9% (95% CI, 74.6-84.2) in the KdD group and 74.4% (95% CI, 65.9-81.1) in the Kd group.

Safety:

308 patients in the KdD group and 153 in the Kd group received at least 1 dose of study treatment. Median treatment duration was 70.1 weeks (IQR, 28.1-77.1) in the KdD group and 40.3 weeks (IQR, 15.3-71.4) in the Kd group.

All-grade treatment-emergent AEs occurred in 306 (99.4%) of 308 patients in the KdD group and 147 (96.1%) of 153 patients in the Kd group. Grade 3 or higher (82.1% in KdD group and 73.9% in Kd group) and serious AEs (56.2% and 45.8%) were reported. Common all-grade AEs (20% preferred term in either group) were thrombocytopenia, anaemia, diarrhea, hypertension, upper respiratory tract infection, fatigue, and dyspnea; of these, thrombocytopenia (37.3% in KdD group and 29.4% Kd group), diarrhea (31.5 and 14.4), upper respiratory tract infection (29.2 and 22.9), and fatigue (24.4 and 18.3) occurred with a ≥5% higher incidence in the KdD group than the Kd group.

Frequent grade 3 or higher AEs (≥5% preferred term in either group) were thrombocytopenia, hypertension, anaemia, pneumonia, neutropenia, fatigue, and lymphopenia. Grade 3 or higher AEs with at least a 2% higher incidence in the KdD than Kd group were thrombocytopenia, hypertension, neutropenia, anaemia, fatigue, pneumonia, influenza, sepsis, and diarrhea. Grade 3 or higher AEs of interest included acute renal failure (2.9% in KdD group and 6.5% in Kd group), cardiac failure (3.9% and 8.5%), ischemic heart disease (2.9% and 2.6%), respiratory tract infections (28.9% and 15.7%), peripheral neuropathy (1% and 0%), daratumumab-related infusion reactions (2.3% and 0%), and viral infections (6.2% and 2.0%).

The frequency of AEs leading to treatment discontinuation was 22.4% in the KdD and 24.8% in the Kd group. Overall, 98 patients (21.3%) discontinued carfilzomib due to AEs. AEs leading to carfilzomib discontinuation occurred in 21.1% of patients in the KdD group and 21.6% of patients in the Kd group. AEs leading to daratumumab discontinuation occurred in 9.1% of patients. Cardiac failure (KdD, 1.9% and Kd, 2.0%) and pneumonia (1.3% and 0%) were the most common AEs leading to carfilzomib and daratumumab discontinuation, respectively. AEs resulted in dose reductions in 38.6% of patients in the KdD group and 34.6% of patients in the Kd group. AEs leading to carfilzomib dose reduction were reported in 77 (25%) of patients in the KdD group and 30 (19.6%) of patients in the Kd group. Dose modification for adverse events consisted of dose delays and not dose reductions for daratumumab. Daratumumab dose delays occurred in 88 (28.6%) of patients in the KdD group.

Treatment-emergent fatal adverse events occurred in 30 (9.7%) patients in the KdD group and 8 (5.2%) patients in the Kd group. Five deaths were reported as treatment-related, all in the KdD group (pneumonia; sepsis with development of *Clostridium difficile* enterocolitis; septic shock in the setting of Pneumocystis pneumonia; Acinetobacter infection; and cardio-respiratory arrest [n=1 each]). Among patients 65 years of age, rates of treatment-emergent fatal AEs was 13.7% in the KdD group and 2.6% in the Kd group. Among patients defined by the investigator as intermediate fit, rates of treatment-emergent fatal AEs was 18.9% in the KdD group and 2.9% in the Kd group (the number of frail patients was low). For the 11 patients with intermediate fit status who had fatal AE, no hypertension or cardiac adverse events were reported in either treatment arm prior to the fatal event. Out of the 21 patients 65 years of age who had fatal event, 2 patients reported cardiac failure and two patients reported hypertension events in the KdD arm.

Rates of exposure-adjusted grade 3 or higher, serious, and fatal AEs were calculated to adjust for differences in treatment duration between treatment groups. The exposure-adjusted risk estimates (per 100 patient-years) were 195.8 in the KdD group and 172.5 in the Kd group (risk ratio, 1.1) for grade 3 or higher AEs, 75.9 and 73.4 (risk ratio, 1.0) for serious AEs, and 9.1 and 6.2 (risk ratio, 1.5) for fatal AEs.

REFERENCES

1. Paquin et al. Overall survival of transplant eligible patients with newly diagnosed multiple myeloma: comparative effectiveness analysis of modern induction regimens on outcome. *Blood Cancer J* 2018; 8:125.
2. Kumar, et al. Improved survival in multpile myeloma and the impact of novel therapies. *Blood* 2008; 111:2516-20.
3. Dimopoulos, et al. Carfilzomib or bortezomib in relapsed or refractory multiple myeloma (ENDEAVOR): an interim overall survival analysis of an open-label, randomised, phase 3 trial. *Lancet Oncol* 2017; 18:1327-37.
4. Sonneveld, et al. How have evolutions in strategies for the treatment of relapsed/refractory multiple myeloma translated into improved outcomes for patients? *Crit Rev Oncol Hematol* 2017; 112:153-70.
5. Nijhof, et al. Current and new therapeutic strategies for relapsed and refractory multiple myeloma: an update. *Drugs* 2018; 78:19-37.
6. Facon, et al. Final analysis of survival outcomes in the phase 3 FIRST trial of up-front treatment for multiple myeloma. *Blood* 2018; 131:301-10.
7. Attal, et al; IFM Investigators. Lenalidomide maintenance after stem-cell transplantation for multiple myeloma. *N Engl J Med* 2012; 366:1782-91.
8. McCarthy, et al. Lenalidomide maintenance after autologous stem-cell transplantation in newly diagnosed multiple myeloma: a meta-analysis. *J Clin Oncol* 2017; 35:3279-89.
9. Pulte, et al. FDA approval summary: Lenalidomide as maintenance therapy after autologous stem cell transplant in newly diagnosed multiple myeloma. *Oncologist* 2018; 23:734-9.
10. Richardson, et al; OPTIMISMM Trial Investigators. Pomalidomide, bortezomib, and dexamethasone for patients with relapsed or refractory multiple myeloma previously treated with lenalidomide (OPTIMISMM): a randomised, open-label, phase 3 trial; *Lancet Oncol* 2019; 20:781-94.
11. Moreau, et al. Treatment of patients with multiple myeloma progressing on frontline-therapy with lenalidomide. *Blood Cancer J* 2019; 9:38.
12. Obeng, et al. Proteasome inhibitors induce a terminal unfolded protein response in multiple myeloma cells. *Blood* 2006; 107:4907-16.
13. United States Food and Drug Administration. Kyprolis: Product Information. Bethesda, MD: US FDA; 2016.
14. European Medicines Agency. Kyprolis: Product Information. London, UK: EMA; 2016.
15. Kyprolis® (carfilzomib) [package insert]. Thousand Oaks, CA: Amgen, Inc.; 2018.
16. Stewart, et al. Carfilzomib, lenalidomide, and dexamethasone for relapsed multiple myeloma. *N Engl J Med* 2015; 372:142-52.
17. Dimopoulos, et al. Carfilzomib and dexamethasone versus bortezomib and dexamethasone for patients with relapsed or refractory multiple myeloma (ENDEAVOR): a randomised, phase 3, open-label, multicentre study. *Lancet Oncol* 2016; 17:27-38.
18. Moreau, et al. Once weekly versus twice weekly carfilzomib dosing in patients with relapsed and refractory multiple myelom (A.R.R.O.W.): interim analysis results of a randomised, phase 3 study. *Lancet Oncol* 2018; 19:953-64.
19. Overdijk, et al. Antibody-mediated phagocytosis contributes to the anti-tumor activity of the therapeutic antibody daratumumab in lymphoma and multiple myeloma. *MAbs* 2015; 7:311-21.
20. Dimopoulos, et al; POLLUX Investigators. Daratumumab, lenalidomide, and dexamethasone for multiple myeloma. *N Engl J Med* 2016; 375:1319-31.
21. Usmani, et al. Clinical efficacy of daratumumab monotherapy in patients with heavily pretreated relapsed or refractory multiple myeloma. *Blood* 2016; 128:37-44.
22. Palumbo, et al; CASTOR Investigators. Daratumumab, bortezomib, and dexamethasone for multiple myeloma. *N Engl J Med* 2016; 375:754-66.
23. DARZALEX™ (daratumumab) injection, for intravenous use [package insert]. Horsham, PA: Janssen Biotech, Inc.; 2018.
24. Chari, et al. Daratumumab plus carfilzomib and dexamethasone in patients with relapsed or refractory multiple myeloma. *Blood* 2019; 134:421-31.
25. Kumar, et al. International Myeloma Working Group consensus criteria for response and minimal residual disease assessment in multiple myeloma. *Lancet Oncol* 2016; 17:e328-46.
26. Spencer, et al. Daratumumab plus bortezomib and dexamethasone versus bortezomib and dexamethasone in relapsed or refractory multiple myeloma: updated analysis of CASTOR. *Haematologica* 2018; 103:2079-87.
27. Martinez-Lopez, et al. Prognostic value of deep sequencing method for minimal residual disease detection in multiple myeloma. *Blood* 2014; 123:3073-9.
28. Kazandjian, et al. Remission and progression-free survival in patients with newly diagnosed multiple myeloma treated with carfilzomib, lenalidomide, and dexamethasone: five-year follow-up of a phase 2 clinical trial. *JAMA Oncol* 2018; 4:1781-3.
29. Drayson, et al. Levofloxacin prophylaxis in patients with newly diagnosed myeloma (TEAMM): A multicenter, double-blind, placebo-controlled, randomised, phase 3 trial. *Lancet Oncol* 2019; 20:1760-1772.

30. Usmani S Z. Efficacy of daratumumab in combination with standard of care regimens in lenalidomide-exposed or -refractory patients with relapsed/refractory multiple myeloma (RRMM): analysis of the castor, pollux, and MMY1001 studies. *Blood* 2018; 132:3288.

31. Moreau, et al. Impact of prior treatment on patients with relapsed multiple myeloma treated with carfilzomib and dexamethasone vs bortezomib and dexamethasone in the phase 3 ENDEAVOR study. *Leukemia* 31:115-122.

What is claimed:

1. A method of treating relapsed or refractory multiple myeloma in a subject suffering therefrom comprising administering to the subject a therapeutically effective amount of a triplet therapy of (a) carfilzomib; (b) daratumumab; and (c) dexamethasone,
  wherein the subject had previously been treated with at least 1 line of treatment, and
  the triplet therapy is administered in cycles of 4 weeks and carfilzomib is administered on day 1 and day 2 of a first cycle at a dose of 20 mg/m$^2$, then at a twice weekly dose of 56 mg/m$^2$ for week 2 and week 3 with a one week dosing holiday, and at a twice weekly dose of 56 mg/m$^2$ for three weeks and a one week dosing holiday during subsequent cycles.

2. The method of claim 1, wherein the subject had previously been on a lenalidomide treatment, a bortezomib treatment, or both.

3. The method of claim 1, wherein the subject exhibits longer progression-free survival, compared to a subject on a doublet therapy of carfilzomib and dexamethasone alone.

4. The method of claim 1, wherein the subject administered the triplet therapy exhibits higher minimal residual disease (MRD) negative-complete response rate, compared to a subject on a doublet therapy of carfilzomib and dexamethasone alone.

5. The method of claim 4, wherein the subject administered the triplet therapy exhibits a MRD negative-complete response rate that is at least 5 times higher than that of a subject on the doublet therapy of carfilzomib and dexamethasone alone.

6. The method of claim 1, wherein a risk of progression or death is lower for a subject administered the triplet therapy, compared to a subject on a doublet therapy of carfilzomib and dexamethasone alone.

7. The method of claim 1, wherein carfilzomib is administered via infusion.

8. The method of claim 1, wherein daratumumab is administered according to a dosing regimen of:
- (i) a dose of 8 mg/kg on day 1 and day 2 of week 1 of a first 4-week cycle,
- (ii) a dose of 16 mg/kg once weekly for weeks 2, 3, and 4 of the first 4-week cycle,
- (iii) a dose of 16 mg/kg once weekly for all doses of a second 4-week cycle,
- (iv) a dose of 16 mg/kg once every two weeks for all doses for 4-week cycles 3, 4, 5, and 6, and
- (v) a dose of 16 mg/kg once every four weeks for each 4-week cycle thereafter.

9. The method of claim 1, wherein the dexamethasone is administered orally.

10. The method of claim 1, wherein the dexamethasone is administered intravenously.

11. The method of claim 1, wherein the dexamethasone is administered at a dose of 20 mg or 40 mg weekly.

12. The method of claim 11, wherein the subject is 75 years old or older and is administered dexamethasone at a dose of 20 mg weekly.

13. The method of claim 11, wherein the dexamethasone dose is 40 mg weekly and is administered in successive days in two divided doses of 20 mg each.

14. The method of claim 13, wherein the dexamethasone is administered 30 minutes to 4 hours before the carfilzomib.

15. The method of claim 14, wherein the daratumumab is administered after the carfilzomib.

16. The method of claim 7, wherein carfilzomib is administered via infusion over 30 minutes.

17. The method of claim 2, wherein the subject is refractory to at least one of the lenalidomide treatment and bortezomib treatment.

18. The method of claim 1, wherein the subject is refractory to at least one of the lenalidomide treatment and bortezomib treatment, and the subject administered the triplet therapy exhibits higher minimal residual disease (MRD) negative-complete response rate, compared to a subject on a doublet therapy of carfilzomib and dexamethasone alone.

* * * * *

```
                          SEQUENCE LISTING

<160> NUMBER OF SEQ ID NOS: 4

<210> SEQ ID NO 1
<211> LENGTH: 122
<212> TYPE: PRT
<213> ORGANISM: Artificial Sequence
<220> FEATURE:
<223> OTHER INFORMATION: VH of daratumumab

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: VL of daratumumab

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 3
<211> LENGTH: 452
<212> TYPE: PRT
<213> ORGANISM: Artificial Sequence
```

<220> FEATURE:
<223> OTHER INFORMATION: HC of daratumumab

<400> SEQUENCE: 3

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

-continued

```
Pro Val Leu Asp Ser Asp Gly Ser Phe Phe Leu Tyr Ser Lys Leu Thr
            405             410             415

Val Asp Lys Ser Arg Trp Gln Gln Gly Asn Val Phe Ser Cys Ser Val
            420             425             430

Met His Glu Ala Leu His Asn His Tyr Thr Gln Lys Ser Leu Ser Leu
        435             440             445

Ser Pro Gly Lys
    450

<210> SEQ ID NO 4
<211> LENGTH: 214
<212> TYPE: PRT
<213> ORGANISM: Artificial Sequence
<220> FEATURE:
<223> OTHER INFORMATION: LC of daratumumab

<400> SEQUENCE: 4

Glu Ile Val Leu Thr Gln Ser Pro Ala Thr Leu Ser Leu Ser Pro Gly
1               5               10              15

Glu Arg Ala Thr Leu Ser Cys Arg Ala Ser Gln Ser Val Ser Ser Tyr
            20              25              30

Leu Ala Trp Tyr Gln Gln Lys Pro Gly Gln Ala Pro Arg Leu Leu Ile
        35              40              45

Tyr Asp Ala Ser Asn Arg Ala Thr Gly Ile Pro Ala Arg Phe Ser Gly
    50              55              60

Ser Gly Ser Gly Thr Asp Phe Thr Leu Thr Ile Ser Ser Leu Glu Pro
65              70              75              80

Glu Asp Phe Ala Val Tyr Tyr Cys Gln Gln Arg Ser Asn Trp Pro Pro
            85              90              95

Thr Phe Gly Gln Gly Thr Lys Val Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
    195             200             205

Phe Asn Arg Gly Glu Cys
    210
```